US011457910B1

(12) United States Patent
Lynch et al.

(10) Patent No.: US 11,457,910 B1
(45) Date of Patent: Oct. 4, 2022

(54) SURGICAL SHIM

(71) Applicant: NuVasive, Inc., San Diego, CA (US)

(72) Inventors: Kelli Lynch, San Diego, CA (US); Stephanie Hagan, San Diego, CA (US); Michael Brotman, San Diego, CA (US); Alejandro R. De La Rosa, National City, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 17/390,448

(22) Filed: Jul. 30, 2021

(51) Int. Cl.
*A61B 17/02* (2006.01)

(52) U.S. Cl.
CPC .... *A61B 17/025* (2013.01); *A61B 2017/0256* (2013.01)

(58) Field of Classification Search
CPC .......... A61B 17/025; A61B 2017/0256; A61B 17/0206; A61B 1/32
USPC .................................................. 600/201–246
See application file for complete search history.

(56) References Cited

U.S. PATENT DOCUMENTS

| 7,905,840 | B2 | 3/2011 | Pimenta et al. |
|---|---|---|---|
| 8,137,284 | B2 | 3/2012 | Miles et al. |
| 10,653,308 | B2 | 5/2020 | Pimenta |
| 2013/0190575 | A1* | 7/2013 | Mast ................... A61B 17/7079 600/215 |
| 2013/0237767 | A1 | 9/2013 | Nunley |
| 2014/0135584 | A1 | 5/2014 | Lee et al. |
| 2015/0088030 | A1 | 3/2015 | Taylor |
| 2019/0209155 | A1 | 7/2019 | Mast |
| 2021/0007727 | A1 | 1/2021 | Riemhofer |

OTHER PUBLICATIONS

FDA Report, PTP Intradiscal Shim (accessed Jul. 22, 2021).
TeDan Surgical Innovations, Phantom XL Ring Retractor System (2013).
Zimmer Biomet, Timberline Lateral Fusion System (2019).

* cited by examiner

*Primary Examiner* — Eduardo C Robert
*Assistant Examiner* — Christina Negrellirodriguez
(74) *Attorney, Agent, or Firm* — Seager, Tufte & Wickhem, LLP

(57) ABSTRACT

A retractor includes retractor blades and one or more shims coupled to one or more of the retractor blades. The shims can include features configured to fasten the shim to vertebral anatomy. Such features can facilitate the use a K-wire or barbed features. Example disclosed shim designs include those featuring a K-wire feature, a barbed feature, and a K-wire with barb design.

40 Claims, 18 Drawing Sheets

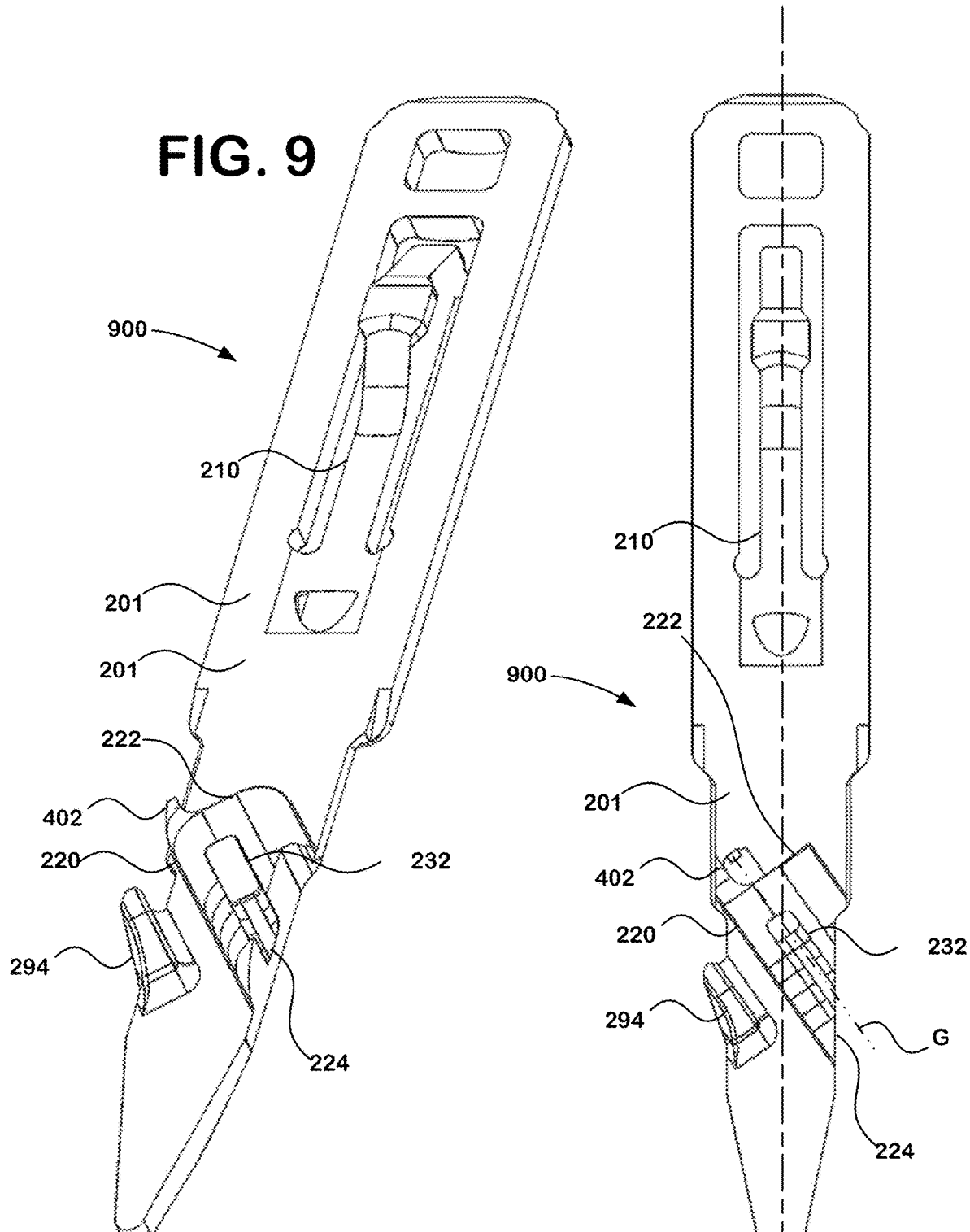

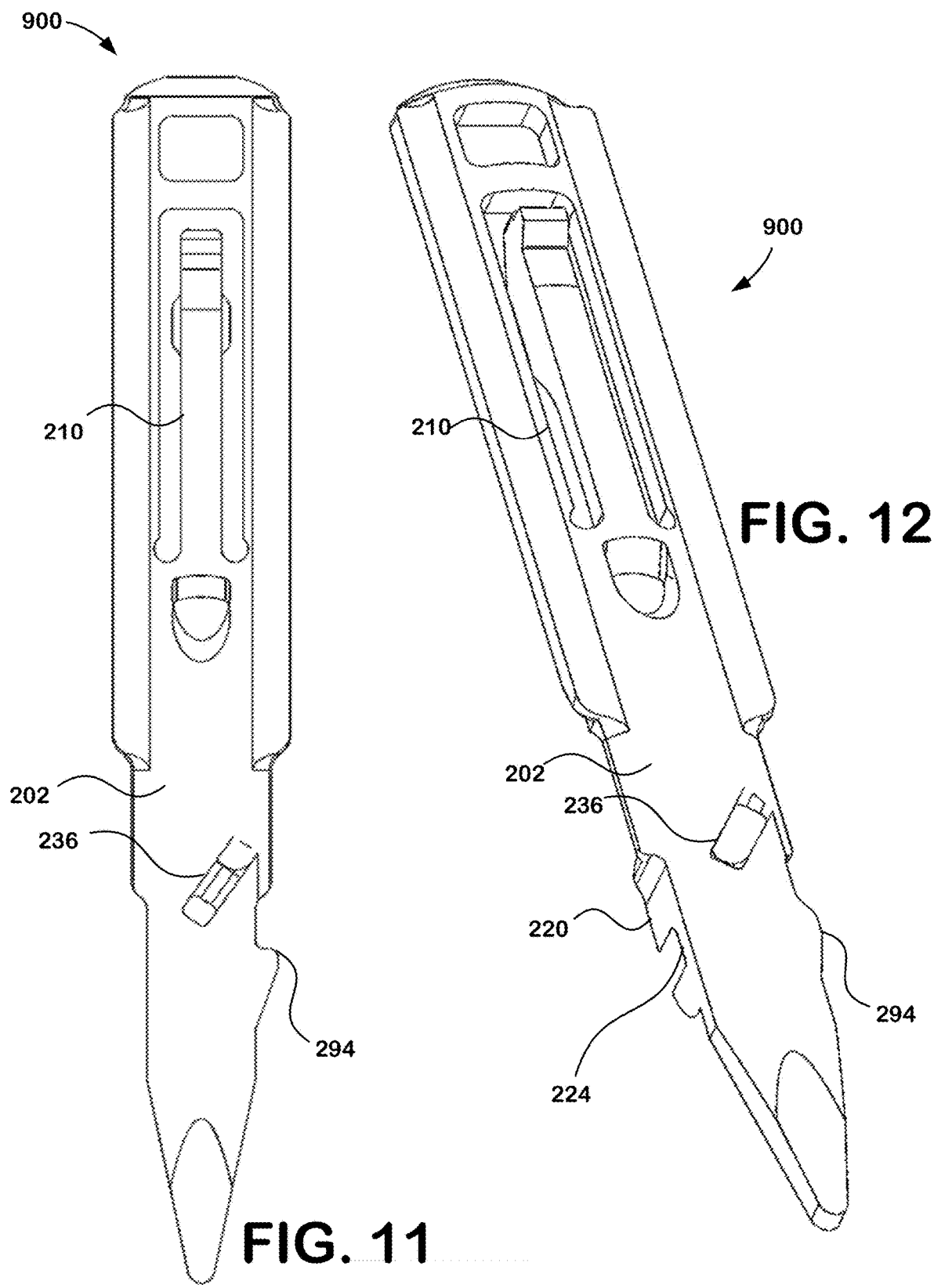

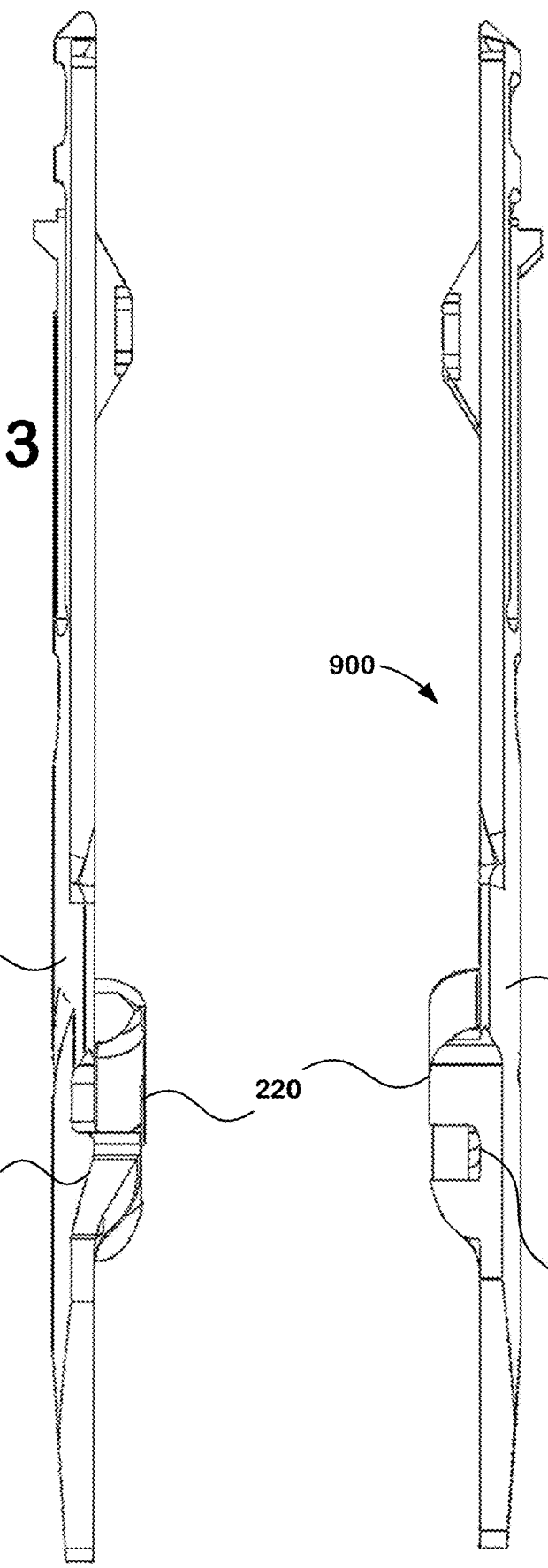

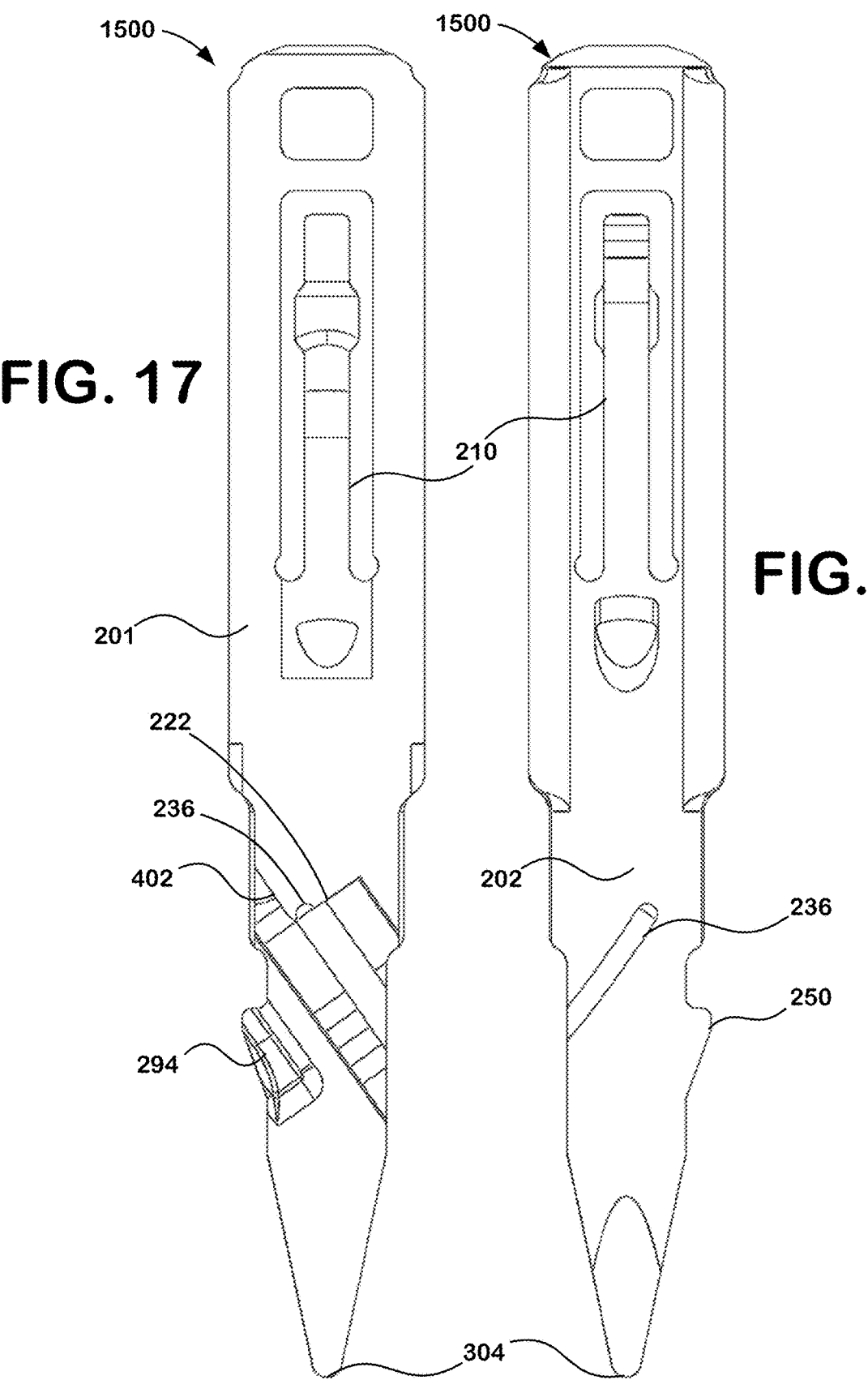

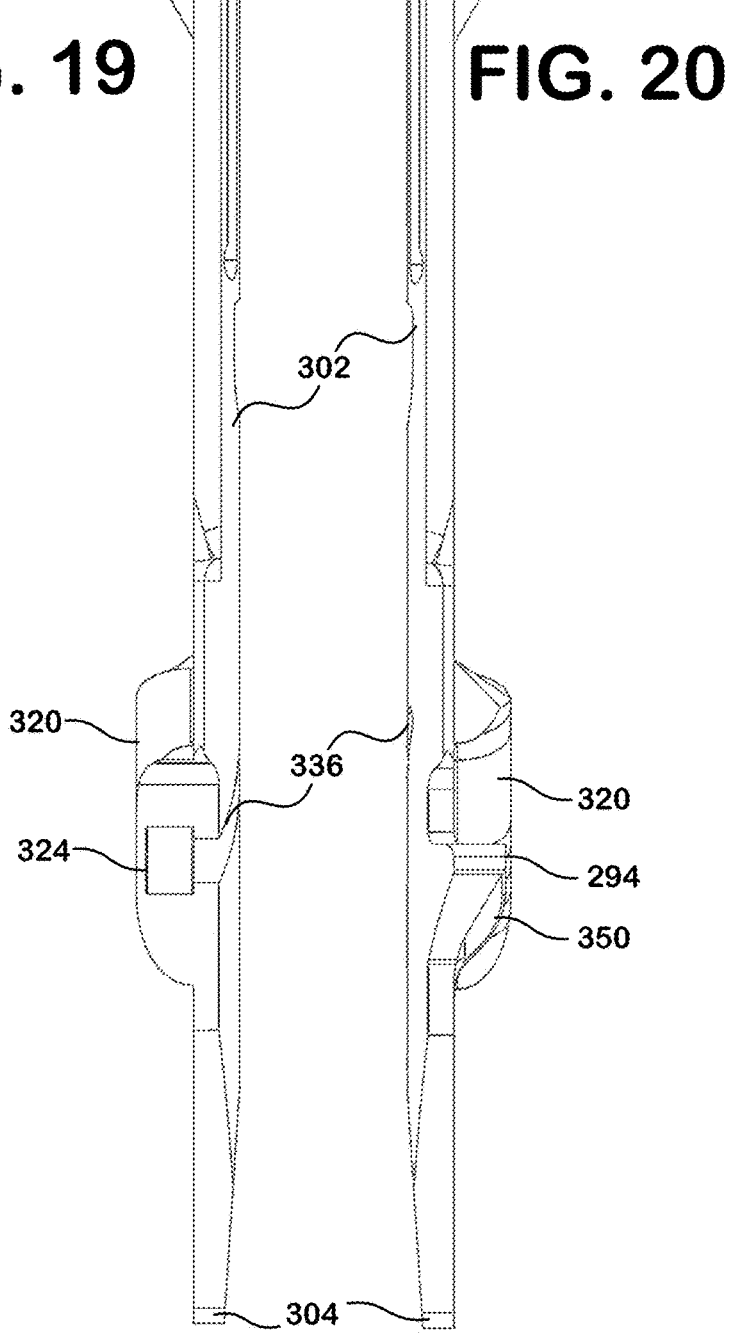

2200

```
┌─────────────────────────────────────────────┐
│ Forming the guide through one or both of a front │
│       opening and a back opening 2210       │
└─────────────────────────────────────────────┘
                      │
                      ▼
┌─────────────────────────────────────────────┐
│        Forming additional features 2212     │
└─────────────────────────────────────────────┘
```

FIG. 22

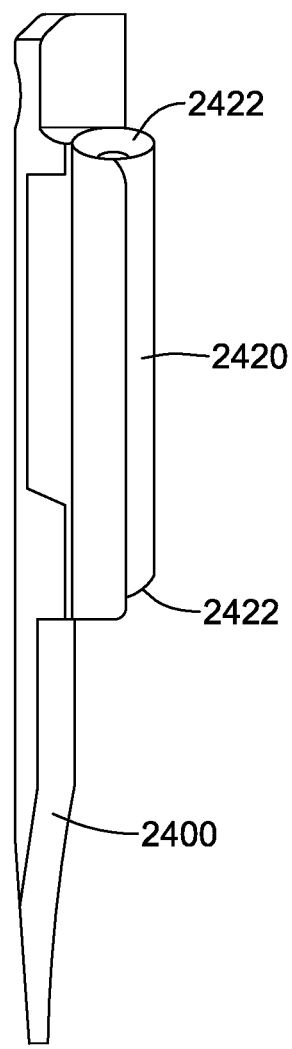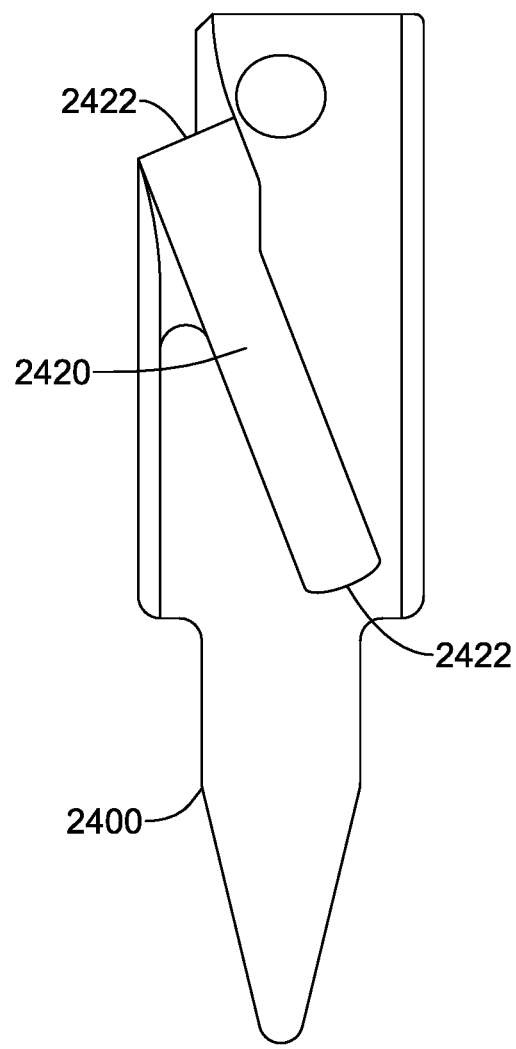
FIG. 24
Prior Art
FIG. 25
Prior Art

SURGICAL SHIM

BACKGROUND

A noteworthy trend in the medical community is the move away from performing surgery via traditional "open" techniques in favor of minimally invasive or minimal access techniques. Open surgical techniques are generally undesirable in that they typically require large incisions and high amounts of tissue displacement to gain access to the surgical target site, which produces concomitantly higher amounts of pain, lengthened hospitalization, and higher morbidity in the patient population. Less-invasive surgical techniques (including so-called "minimal access" and "minimally invasive" techniques) are gaining favor due to the fact that they involve accessing the surgical target site via incisions of substantially smaller size with greatly reduced tissue displacement requirements. This, in turn, reduces the pain, morbidity, and cost associated with such procedures.

Less-invasive surgical access systems often include retractors used to form and expand a surgical corridor. Shims can be used to enhance capabilities of retraction assemblies, such as is described in U.S. Pat. No. 7,905,840 (filed Oct. 18, 2004); U.S. Pat. No. 8,137,284 (filed Oct. 8, 2003); and US 2021/0007727 (filed Jun. 18, 2020), which are all hereby incorporated herein by reference for any and all purposes. A prior implementation of a shim is shown in FIGS. 24-26.

FIGS. 24, 25, and 26 show side, front, and front-perspective views, respectively, of a first prior implementation of a shim 2400. The shim 2400 has a complete, elongate, and straight tube 2420. The tube 2420 is a cylinder having an opening 2422 in each of the two ends of the cylinder connected by a straight bore surrounded circumferentially by material. The proximal opening 2422 is oval and acts as a funnel. The distal opening 2422 is in the shape of a circle and are the only openings in the tube 2420. The openings 2422 do not extend beyond the ends of the tube 2420. The tube 2420 has a left end, from the perspective of FIG. 25, that extends beyond a left side of the shim 2400. The tube 2420 is disposed on the shim 2400 such that when the distal end of the shim 2400 is disposed in a disc space, the distal end of the elongate tube 2420 does not enter or contact the disc space. The tube 2420 is disposed on the shim 2400 such that the tube 2420 does not extend below a distal end of a retractor to which the shim 2400 is coupled. The tube 2420 does not extend below a distal end of lateral tabs of the shim 2400 that slidably engage the shim 2400 with the retractor blade. As can be seen in FIG. 24, the tube 2420 projects from the shim 2400 in a manner that intrudes on a surgical corridor formed by the retractor blade. A surgeon uses the shim 2400 by inserting a K-wire into a proximal end of the tube 2420 such that the K-wire exits the distal end of the tube 2420 and enters into a vertebral endplate. The tube 2420 controls an angle of the K-wire in a plane parallel to a general plane of the shim 2400 and retractor blade. The distal end of the tube 2420 does not enter or reach the intervertebral disc when in use.

A second prior implementation of a shim lacked features for interacting with a K-wire. Rather, the second prior implementation included a plurality of flat serrations mirrored across a length of the second prior implementation of a shim.

The access systems developed to date, however, fail in various respects to meet all the needs of the surgeon population.

SUMMARY

In a first example, there is a surgical shim that includes a front surface, a back surface opposite the front surface, a retractor connector, and a guide disposed at the front surface. The guide defines a proximal opening, a distal opening, a path from a proximal opening to a distal opening, and a back opening extending through the front surface and the back surface.

The path can extend along a guide axis oblique to a midline axis along the length of the surgical shim. A K-wire can extend through the guide along the path. The guide can further define a front opening. The guide can further include a roof. The guide can further include a proximal wall and a distal wall. The roof can span at least part of the proximal wall and the distal wall. The roof can cover a portion of the back opening. In an example, at least a portion of a floor of the guide between the proximal wall and the distal wall is not covered by the roof. In an example, no portion of the guide along the path is covered by both the floor and the roof when viewed from the front. The distal opening can be disposed proximate a first side of the shim. The surgical shim can further include a barb disposed proximate a second side of the shim opposite the first side. The barb can be the only barb of the shim. The barb can have a proximal side extending parallel to a guide axis of the guide. The proximal side of the barb can have a steeper slope than a distal side of the guide. A maximum height of the barb above the front surface of the shim can be the same as a maximum height of the guide above the front surface of the shim.

In a second example, there is an apparatus that includes a retractor blade and a surgical shim. In an example, the surgical shim includes a front surface, a back surface opposite the front surface, a retractor connector coupled to the retractor blade, and a guide disposed at the front surface and having a floor. The guide can define a proximal opening, a distal opening, a path from a proximal opening to a distal opening, and a back opening through the floor to the back surface. The back opening can be at least partially covered by the retractor blade.

In an example, the apparatus further includes a K-wire extending through the guide along the path. The path can extend along a guide axis oblique to a midline axis of the surgical shim along the length of the surgical shim. The apparatus can further include a retractor. The retractor blade can be coupled to the retractor. The shim can further include a proximal wall, a distal wall, and a roof spanning at least part of the proximal wall and the distal wall. The roof can be disposed so as to not cover the floor when the shim is viewed from the front.

In a third example, there is a method that includes making available for use a surgical shim and a retractor having a retractor blade; placing the retractor blade at a target surgical location; attaching the surgical shim to the retractor blade; advancing the surgical shim into a disc space such that a distal opening of a guide of the surgical shim is disposed within the disc space; advancing a K-wire into a proximal end opening of the guide; advancing the K-wire through the guide and out the distal opening of the guide; expanding an operative corridor with the retractor; and performing a procedure through the operative corridor.

The method can include advancing the K-wire into a vertebral endplate. The procedure can be a prone lateral interbody fusion. Attaching the surgical shim to the retractor blade can be performed such that a back opening of the guide is at least partially blocked by the retractor blade. Advancing the K-wire through the guide and out the distal opening of the guide can include wedging the K-wire in a curved section of the guide.

BRIEF DESCRIPTION OF THE DRAWINGS

FIG. 9 illustrates a front perspective view of a second example shim.

FIG. 10 illustrates a front view of the second example shim of FIG. 9.

FIG. 11 illustrates a back view of the second example shim of FIG. 9.

FIG. 12 illustrates a front perspective view of the second example shim of FIG. 9.

FIG. 13 illustrates a first side view of the second example shim of FIG. 9.

FIG. 14 illustrates a second side view of the second example shim of FIG. 9.

FIG. 17 illustrates a front view of the third example shim of FIG. 15.

FIG. 18 illustrates a back view of the third example shim of FIG. 15.

FIG. 19 illustrates a first side view of the third example shim of FIG. 15.

FIG. 20 illustrates a second side view of the third example shim of FIG. 15.

FIG. 22 illustrates an example method of manufacturing a shim.

FIG. 24 illustrates a side view of a prior shim.

FIG. 25 illustrates a front view of a prior shim.

DETAILED DESCRIPTION

Disclosed shims include features configured to fasten the shim to a vertebral anatomy by guiding a K-wire into a vertebral body via an adjacent vertebral endplate. By increasing the rigidity of the connection between the shim and the spine, greater retractor stabilization can be achieved. The K-wire can be inserted either with the shim, or into the shim after the shim has been installed. The K-wire routes through the shim and into the disc. When ready, the K-wire can be removed on its own, or with the shim. Optionally, the shim can further include one or more barbs to enhance engagement of the shim with an intervertebral disc in which the shim is disposed. The barb designs can be effective by, depending on the height of the disc space, holding into the vertebral body or the fibers of the annulus. The barb shapes can vary from sharp to rounded. The combination of barbs and K-wire features can take advantage of each design feature. The barbs can be located to catch and prevent the blade shim from pulling out (e.g., the barb gets caught on the outer layers of the annulus) while the K-wire is the more robust fixation into the disc. As discussed in more detail below, shims disclosed herein can provide advantages over prior shim designs, including improved ease of manufacturing through front and back openings in the K-wire guide, improved fixation with a barb, and a lower profile that protrudes less into the surgical corridor. Further, entering the endplate can facilitate the k-wire avoiding common pathological interferences (e.g., osteophytes), which can increase usability and improve k-wire grip.

Figure 1:
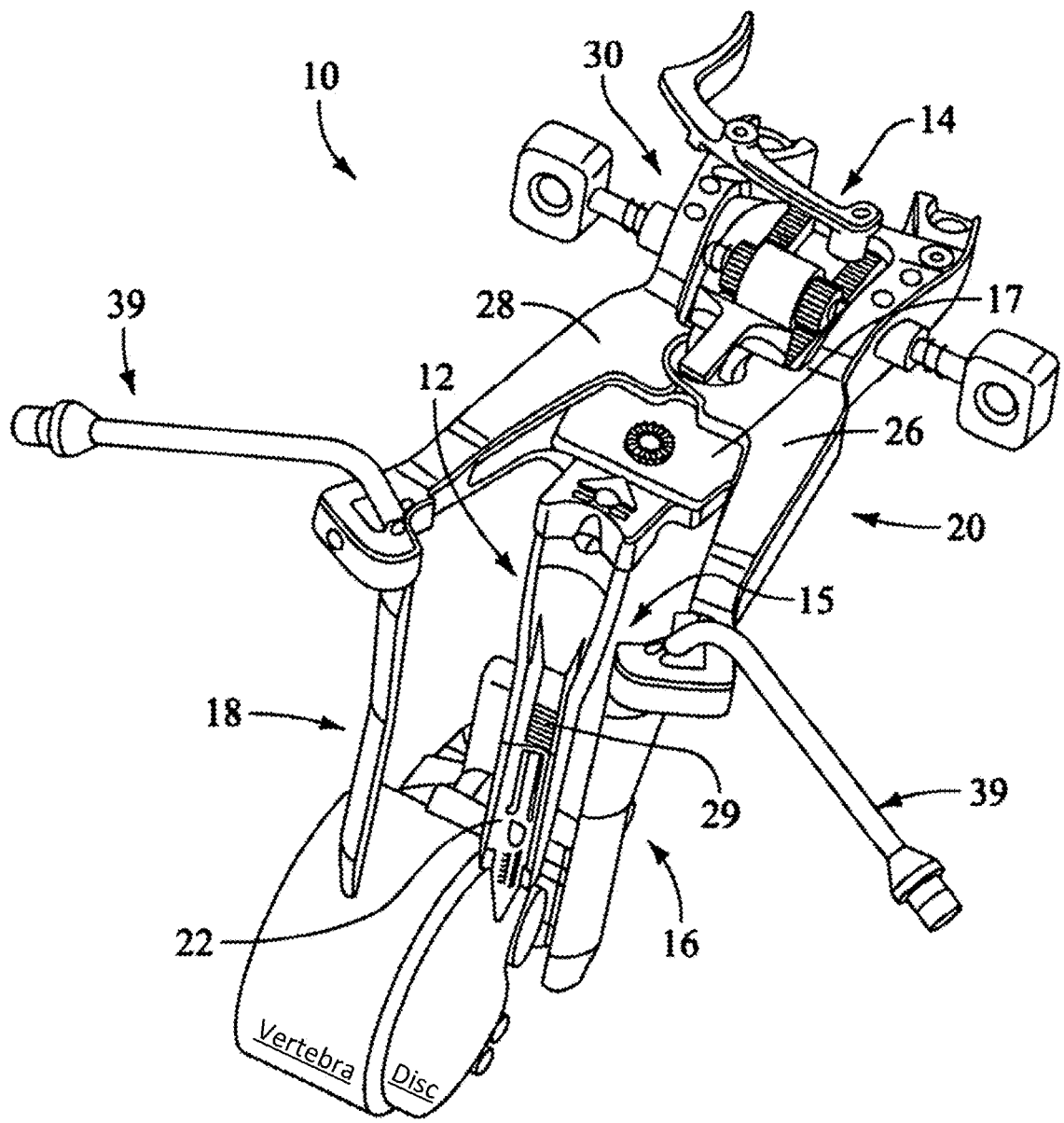
FIG. 1 illustrates a perspective view of an example retractor having a shim inserted into an intervertebral disc space.

FIG. 1 illustrates a tissue retractor 10 forming part of a surgical access system that can benefit from shims disclosed herein. The retractor 10 includes a plurality of retractor blades 12, 16, 18 extending from a handle assembly 20. The illustrated handle assembly 20 is provided with a first retractor blade 12, a second retractor blade 16, and a third retractor blade 18. The retractor 10 is shown in a fully retracted or "open" configuration, with the retractor blades 12, 16, 18 positioned a distance from one another so as to form an operative corridor 15 therebetween and extending to a surgical target site (e.g. an intervertebral disc). Although shown with regard to the three-bladed configuration, the number of retractor blades 12, 16, 18 may be increased or decreased. Moreover, although described and shown here with reference to a generally lateral approach to a spinal surgical target site (e.g., with the first blade 12 being the "posterior" blade, the second blade 16 being the "cephaladmost" blade, and the third blade 18 being the "caudal-most" blade), the retractor 10 of the present invention may find use in any number of different surgical approaches, including generally posterior, generally postero-lateral, generally anterior and generally antero-lateral.

The retractor blades 12, 16, 18 can be equipped with various additional features or components. The illustrated posterior retractor blade 12 is equipped with a surgical shim 22. The shim 22 can serve any of a variety of different purposes, such as facilitating the distraction of adjacent vertebral bodies (thereby restoring disc height), facilitating securing the retractor 10 relative to the surgical target site, and facilitating forming a protective barrier to prevent the ingress or egress of instruments or biological structures (e.g., nerves or vasculature) into or out of the operative corridor. The shim 22 can be implemented using any of the features or combinations of features described in examples herein. The shim 22 can be equipped with a mechanism to selectively and releasably engage with the retractor blades 12, 16, 18. For example, the shim 22 can include a tab configured to engage with corresponding ratchet-like grooves 29 along the inner-facing surfaces of the retractor blades 12, 16, 18. The shim 22 can be provided with a pair of engagers having, for example, a generally dove-tailed cross-sectional shape. The engagers can be dimensioned to engage with receiving portions on the respective retractor blades 12, 16, 18. The shim 22 can be provided with an elongate slot for engagement with an insertion tool. Each tab can be equipped with an enlarged tooth that engages within corresponding grooves 29 provided along the inner surface of the retractor blades 12, 16, 18. Optional light emitting devices 39 may be coupled to one or more of the retractor blades 12, 16, 18 to direct light down the operative corridor 15. Any or all of the retractor blades 12, 16, 18 and shims 22 can be provided with one or more electrodes (e.g., at distal regions thereof) equipped for use with a nerve surveillance system, such as, NVM5 provided by NUVASIVE, INC.

The handle assembly 20 may be coupled to any number of mechanisms for rigidly registering the handle assembly 20 in fixed relation to the operative site, such as through the use of an articulating arm mounted to the operating table. The handle assembly 20 includes first and second arm members 26, 28 hingedly coupled via coupling mechanism 30. The cephalad-most retractor blade 16 is rigidly coupled (e.g., generally perpendicularly) to the end of the first arm member 26. The caudal-most retractor blade 18 can be rigidly coupled (e.g., generally perpendicularly) to the end of the second arm member 28. The posterior retractor blade 12 is rigidly coupled (e.g., generally perpendicularly) to a translating member 17, which is coupled to the handle assembly 20 via a linkage assembly 14. The linkage assembly 14 can be configured to cause one or more of the retractor blades 12, 16, 18 to move (e.g., translate, pivot, or distract) in various ways in response to input from a user.

The retractor 10 described herein is provided as an example. The apparatuses and techniques described herein can be applicable to any of a variety of different retraction assemblies and retractor blades. Other example retractor systems that can benefit from the shims and other features described herein include those retractor systems described in U.S. Pat. Nos. 7,905,840; 8,137,284; and US 2021/0007727, which were all previously incorporated herein by reference. A first example shim that can be used with the retractor 10 or other retractors is shown and described in FIGS. 2-8.

First Example

Figure 2:
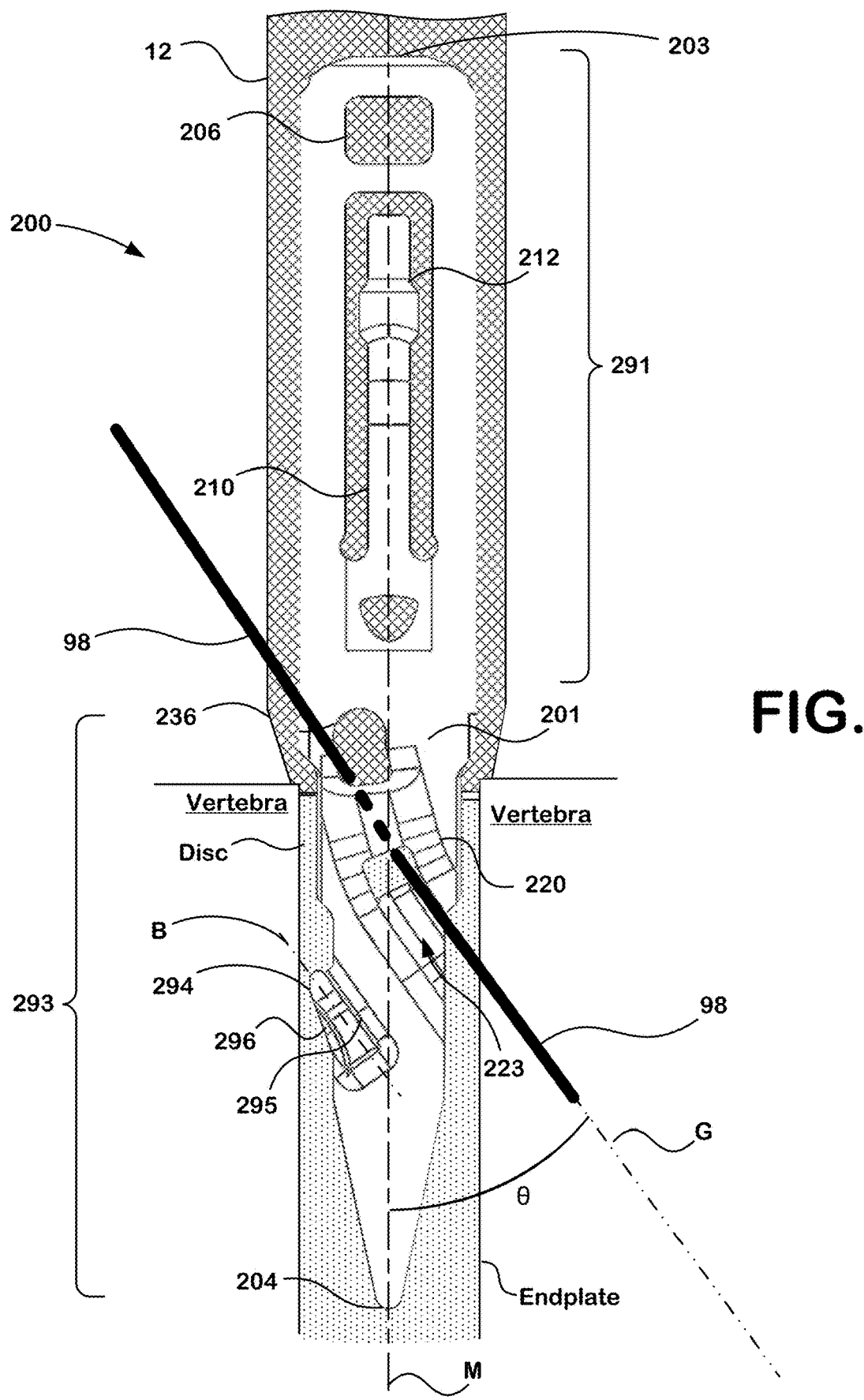
FIG. 2 illustrates a front view of a first example shim inserted into an intervertebral disc space and having a guide that redirects a K-wire.
Figure 3:
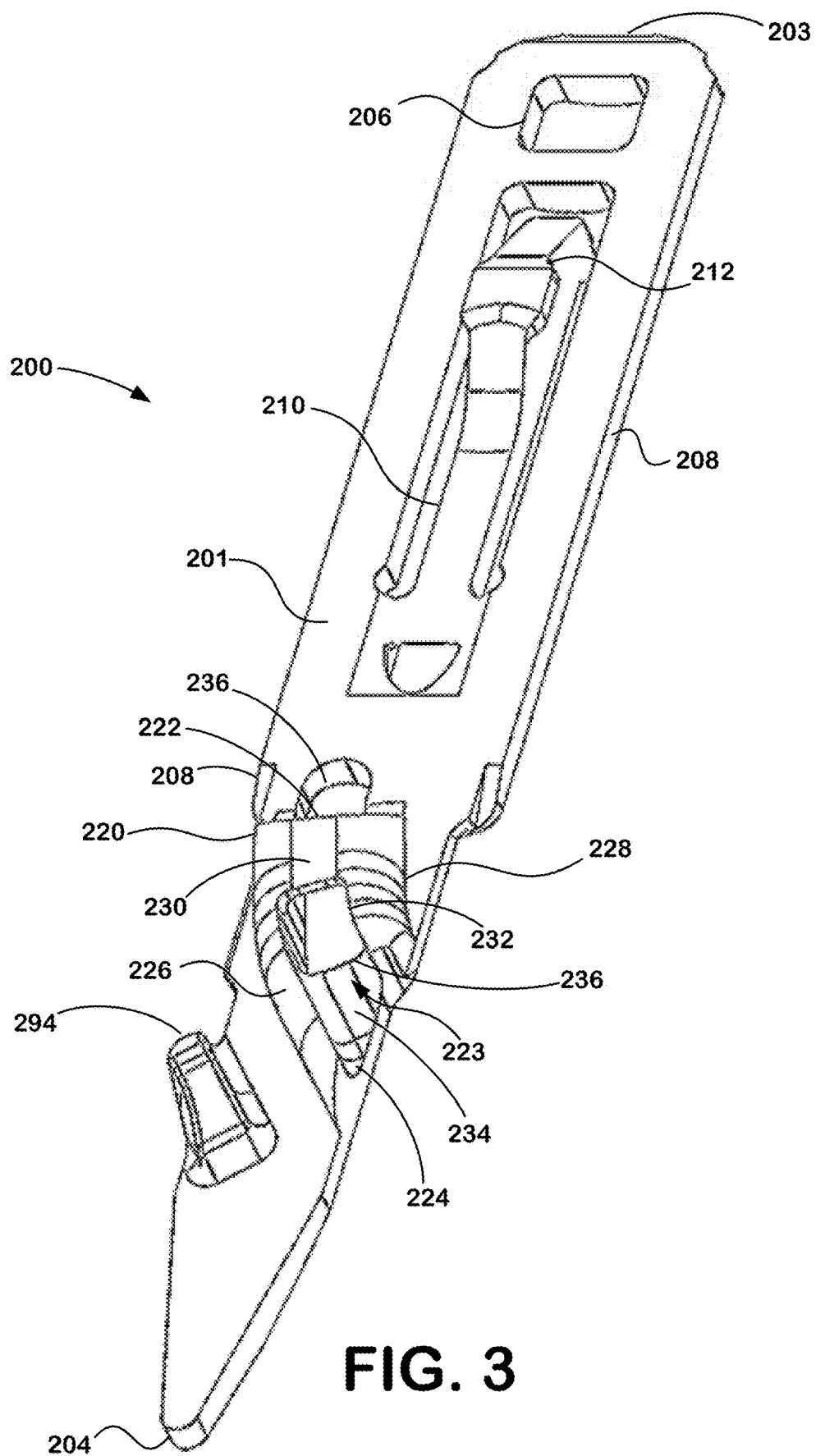
FIG. 3 illustrates a front perspective view of a first example shim of FIG. 2.
Figure 4:
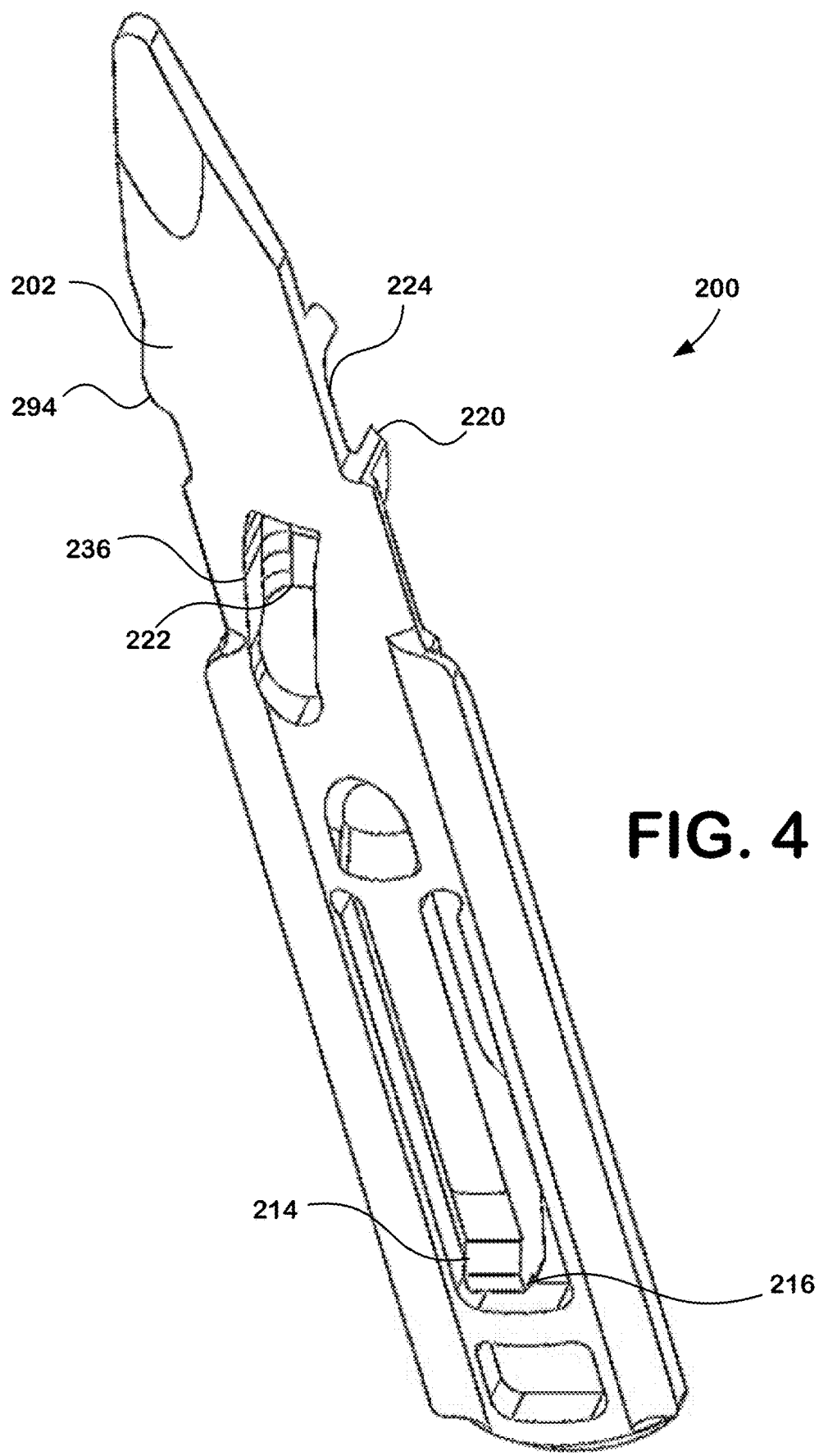
FIG. 4 illustrates a back perspective view of the first example shim of FIG. 2.
Figures 5, 6:
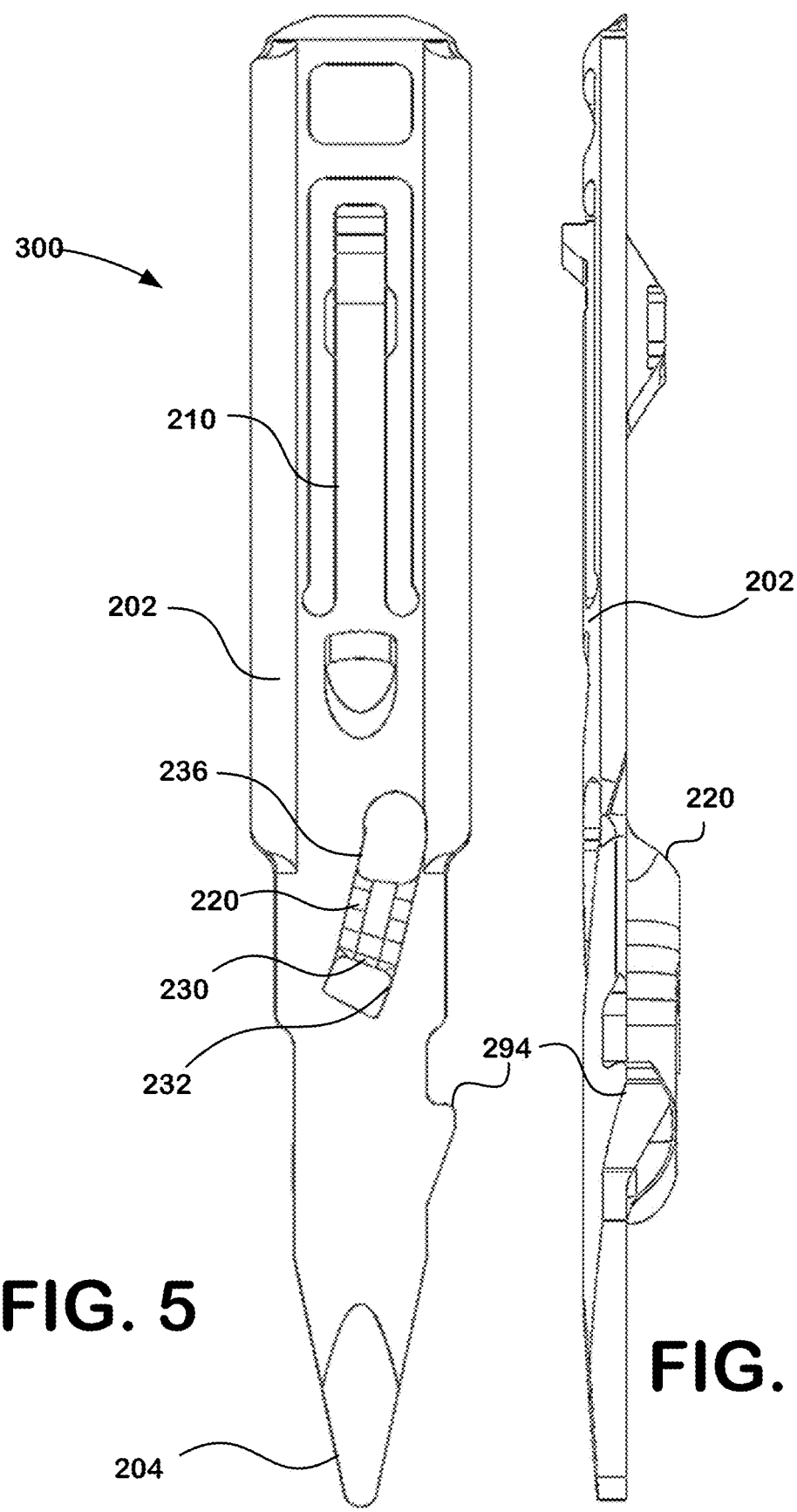
FIG. 5 illustrates a back view of the first example shim of FIG. 2.
FIG. 6 illustrates a first side view of the first example shim of FIG. 2.
Figures 7, 8:
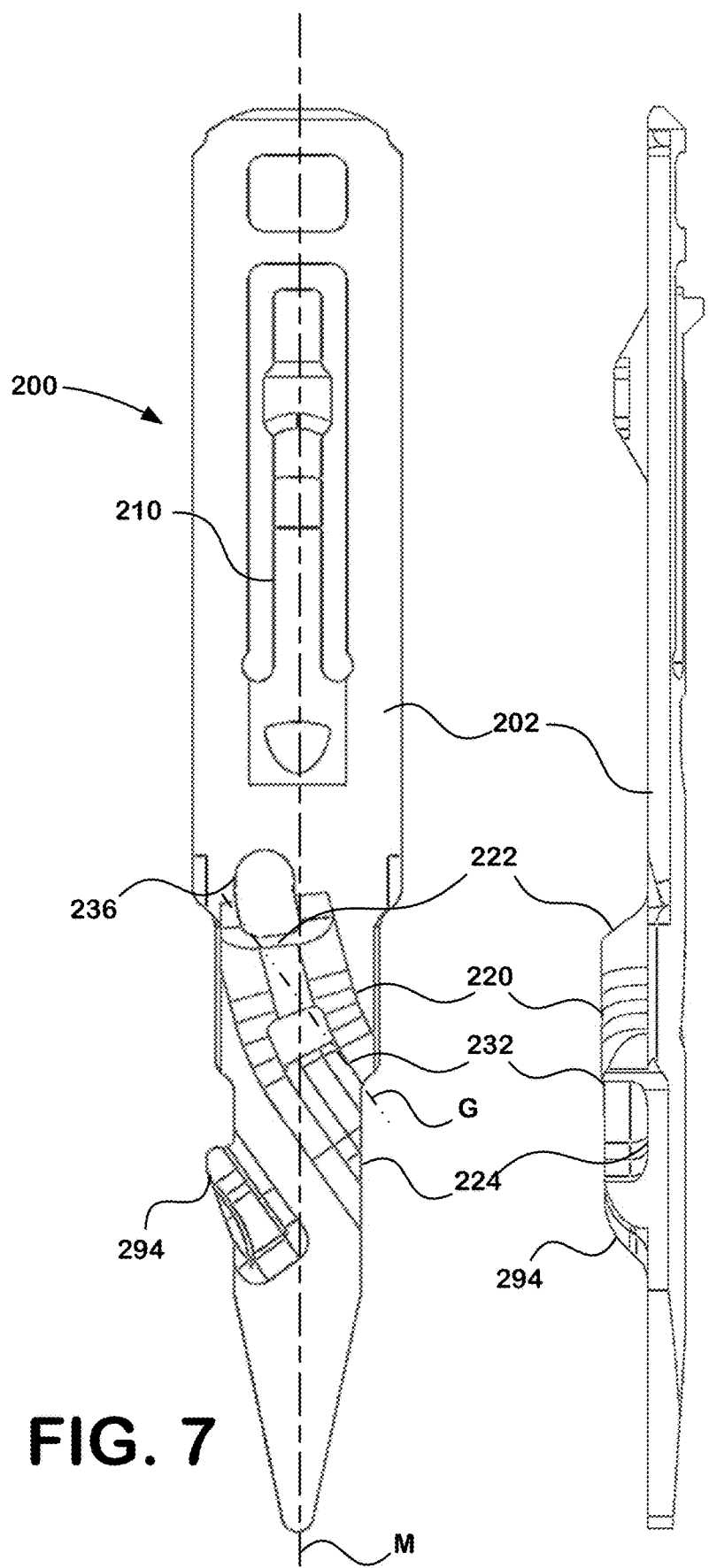
FIG. 7 illustrates a front view of the first example shim of FIG. 2.
FIG. 8 illustrates a second side view of the first example shim of FIG. 2.
Figure 15:
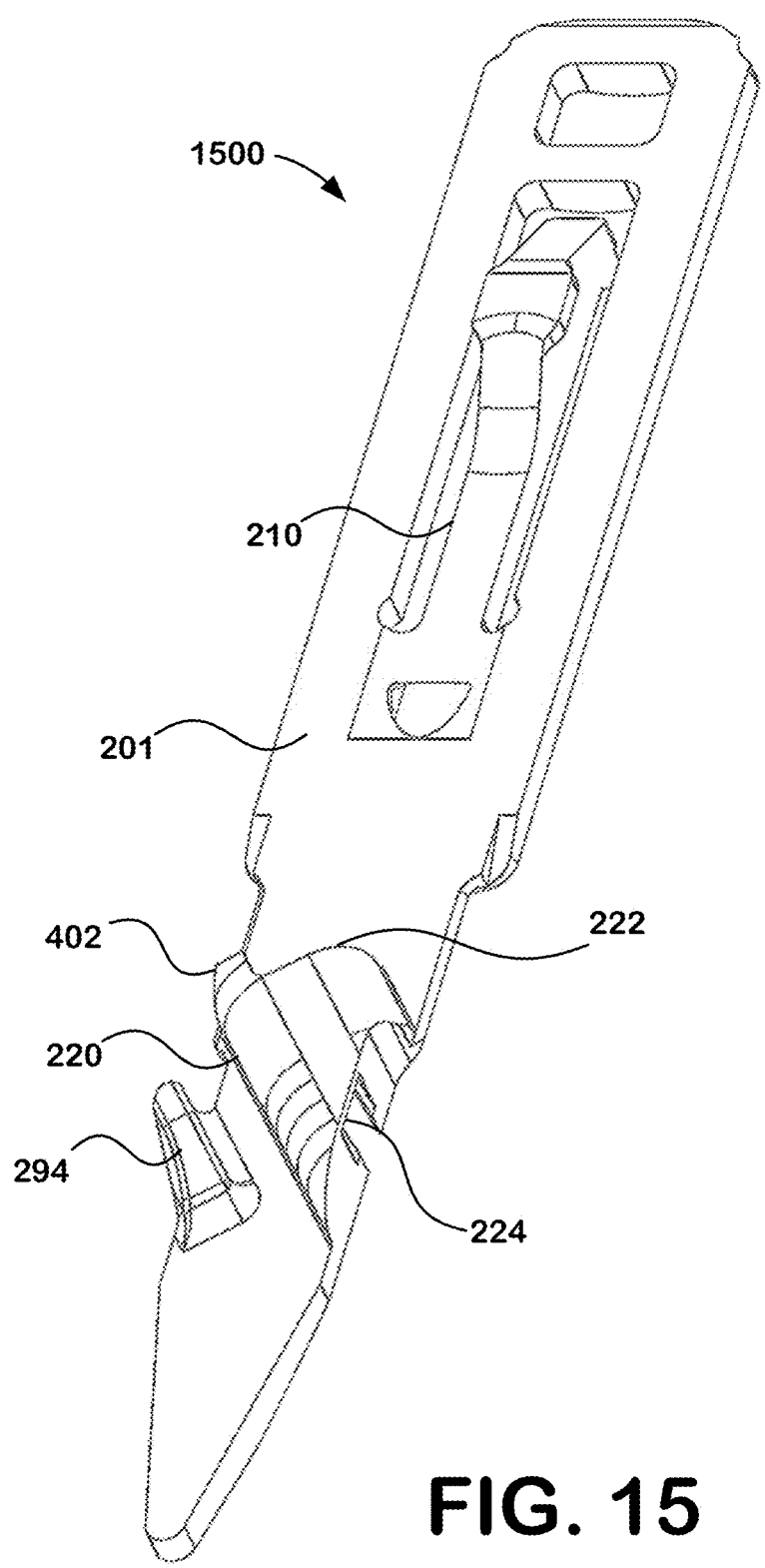
FIG. 15 illustrates a front perspective view of a third example shim.
Figure 16:
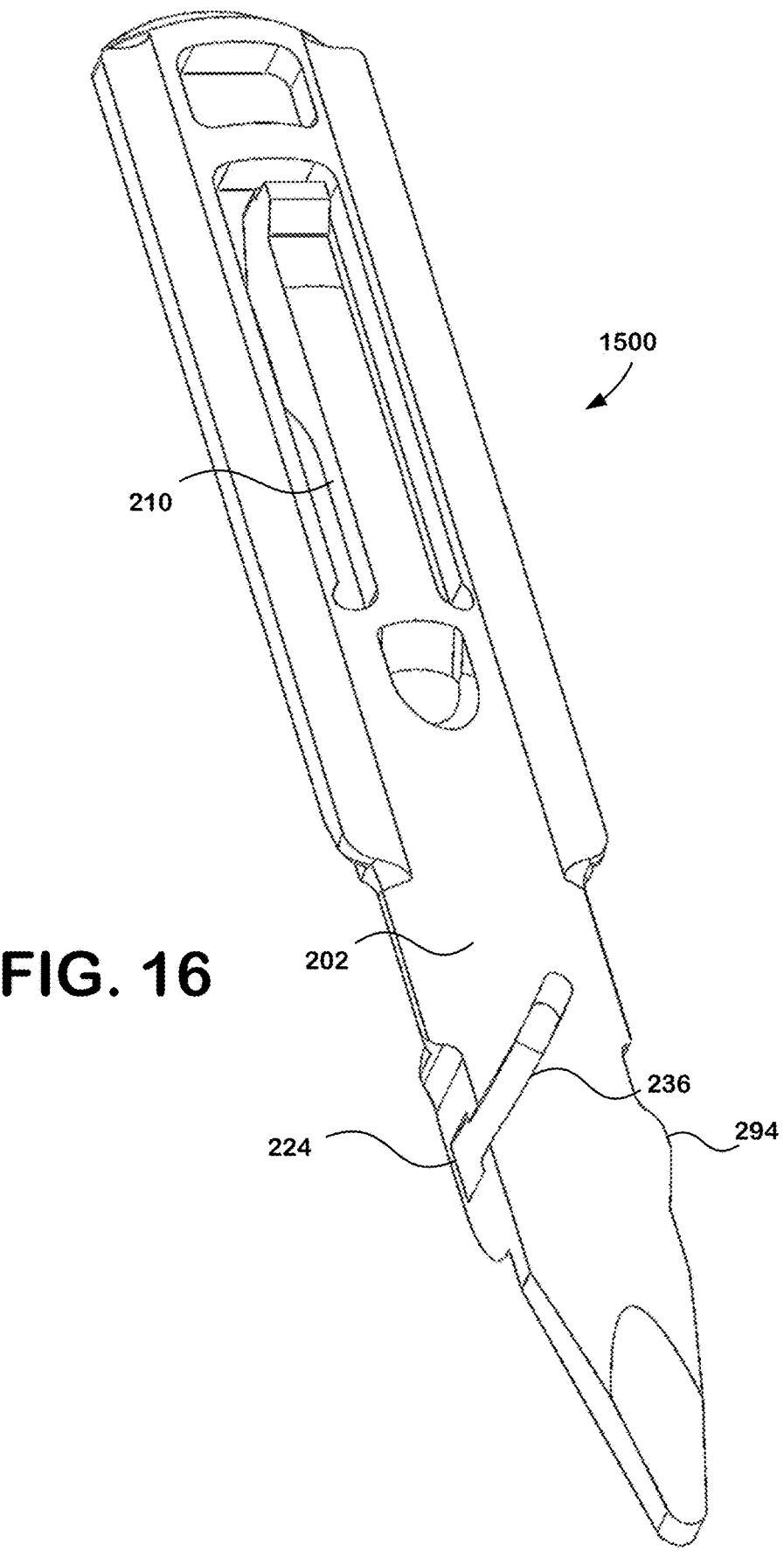
FIG. 16 illustrates a back perspective view of the third example shim of FIG. 15.

FIGS. 2-8 illustrate a first example shim 200. FIG. 2 illustrates a front view of an example shim 200 inserted into a disc space between adjacent vertebrae. The shim 200 has a proximal end 203 opposite a pointed distal end 204 and has a front face 201 opposite a back face 202. The front face 201 of the shim 200 can be the relatively wide (e.g., compared to the thickness of the shim as seen in a side view) and tall (e.g., compared to a view of the shim from the top or bottom) face of the shim that presents to an operative corridor when the shim 200 is used with a retractor blade 12. The back face 202 of the shim can be surface of the shim 200 that presents away from the operative corridor. The back face 202 typically is in contact with or close proximity to a front face of the retractor blade 12 to which the shim 200 is coupled.

The shim 200 includes a retractor connection section 291 having one or more retractor connectors configured to couple with a retractor blade 12 and an anatomy connection section 93 configured to interface with a recipient's anatomy. The one or more retractor connectors can include one or more tabs, teeth, spring-loaded balls (e.g., to cooperate with a detent), or other features configured to couple the shim 200 with the retractor blade 12. In the illustrated example, the proximal portion of the shim 200 includes a central engagement tab 210 that facilitates locking the shim 200 to a retractor blade 12. The engagement tab 210 has a ramped leading edge 214 that allows the shim 200 to advance down indentations on the inner surface of the retractor blade 12 (see, e.g., grooves 29 on retractor blade 12 in FIG. 1). The trailing edge 216 of the engagement tab 210 is squared to prevent disengagement (e.g., thereby resisting unwanted backout of the shim 200) from the indentation without use of a removal tool. The engagement tab 210 also includes a T-shaped removal lip 212 configured to engage a shim removal tool (see, e.g., removal tool of US 2014/0135584, filed Aug. 23, 2011, which is hereby incorporated herein by reference in its entirety for any and all purposes). The T-shaped lip 212 of the engagement tab 210 allows the removal tool to lift the trailing edge 216 away from the retractor blade and remove the shim 200. The locking intradiscal shim 200 has a pair of lateral elongated tab members 208 that are configured to slidably engage elongated slot members that run the length of the inside surface of the retractor blade. The shim 200 includes a cutout 206 located near the proximal end of the shim 200 configured for engagement with a shim removal tool.

The anatomy connection section 293 can include one or more features to facilitate interaction between the shim 200 and the recipient's anatomy, such as a guide 220, one or more barbs 294, one or more serrations, a triangular distal tip, other features, or combinations thereof.

The guide 220 can be a portion of the shim 200 configured to control an angle of a K-wire 98 inserted through the guide 220. As illustrated, the guide 220 directs the K-wire 98 from left to right. In other examples, the guide directs the K-wire from right to left (e.g., mirrored to what is shown). In the example illustrated in FIG. 2, the K-wire 98 enters the guide 220 at an angle substantially parallel to a guide axis G defined by the guide 220. In another example, the K-wire 98 enters the guide 220 along an axis substantially parallel to the midline axis M of the shim 200, and the K-wire exits the guide 220 along a guide axis G that is angled by θ degrees relative to a midline axis M. In the illustrated example, the guide 220 directs the K-wire 98 in two dimensions along a plane substantially parallel to the width of the shim 200 and the retractor 10. In other examples, the guide 220 can direct the K-wire 98 in three directions, such as by the addition of a ramp on the floor 234 or the bottom of the roof 230 to direct the K-wire in a front-back direction in addition to directing the K-wire in a proximal-distal direction and lateral direction. Such an additional direction can further improve fixation.

The distal portion of the shim 200 (e.g., the anatomy connection region 293) includes a guide 220. The guide 220 is a region of the shim 200 configured to receive a K-wire 98 or other instrument. The guide 220 can be configured to control an angle of a K-wire 98 inserted through the guide 220, such as by changing or maintaining a direction of travel of a K-wire 98 inserted through the guide 220. The K-wire 98 can enter through a proximal opening 222 of the guide 220 that is in communication with a distal opening 224 of the guide 220 via a path 223 between the proximal opening 222 and the distal opening 224. The path 223 can extend along a guide axis G oblique to a midline axis M along the length of the surgical shim 200.

The path 223 is sized and shaped to accommodate passage of a K-wire 98. The guide 220 can be configured such that a K-wire 98 can extend through the guide 220 along the path 223. The outside of the guide 220 and the outside of the path 223 are at least partially bounded by the outside and inside portions, respectively, of a distal wall 226 and a proximal wall 228. The distal wall 226 is a wall portion that forms a distal barrier of the guide 220. The distal wall 226 can be a portion configured to contact the K-wire 98 and direct movement of the K-wire 98 laterally as the K-wire 98 is inserted into the guide 220. The proximal wall 228 is a wall portion that forms a proximal barrier of the guide 220 and can resist movement of the K-wire 98.

As illustrated, a roof 230 can connect the proximal wall 228 and the distal wall 226. In other examples, the roof 230 is connected to either the proximal wall 228 or the distal wall 226 but not both (e.g., the roof 230 can be cantilevered out). The roof 230 can be a component configured to resist movement of the K-wire in a direction parallel to the front-back axis of the shim 200. In some examples, the roof 230 covers substantially all of the guide 220. In the illustrated example, the roof 230 covers only a proximal portion of the guide 220, and the guide 220 defines a front opening 232 bounded in part by the distal wall 226, the proximal wall 228, and the roof 230. The roof 230 can be disposed such that the roof 230 does not cover the floor 234 when the shim 200 is viewed from the front.

The guide 220 further defines a floor 234. The floor 234 can be a region of the guide 220 defined between the proximal wall 228 and the distal wall 226. Through the floor 234 is a back opening 236 extending through the front surface and the back surface of the shim 200. The back opening 236 of the floor 234 can extend through the shim 200. The back opening 236 can generally follow the path 223 of the guide 220. The back opening 236 can extend to both sides of the roof 230. The back opening 236 can correspond to a tool path used to form the passage through the guide beneath the roof 230. Portions of the back opening 236 are blind holes with respect to the roof 230 and through holes on either side of the roof 230.

The proximal opening 222 of the guide 220 is disposed proximate a distal end of the elongate tabs 208. In an example, the proximal opening 222 of the guide, when viewed from the front (see FIG. 7) is perpendicular to a long axis of the shim 200. In the illustrated example, the proximal opening 222 is slightly angled relative to perpendicular to the long axis of the shim 200.

The distal opening 224 of the guide 220 is disposed proximate a lateral edge of the shim 200 and is disposed at a region of the shim 200 that is configured to be disposed in an intervertebral disc space during use. In the illustrated example, the distal opening 224 of the guide.

As can be seen, the proximal opening 222 and the distal opening 224 need not be fully enclosed (e.g., need not be bounded on all sides by a portion of the guide). Rather, the openings 222, 224 can correspond to regions of the guide 220 where the guide 220 begins (proximal opening 222) and ends (distal opening 224) substantial control over a K-wire inserted therethrough.

In the illustrated example, the proximal opening 222 is laterally bounded by the proximal wall 228 and the distal wall 226 and is bounded toward the front by the roof 230. However, the shim 200 alone does not substantially bound the proximal opening 222 in a rearward direction due to the presence of the back opening 236. However, when the shim 200 is engaged with a retractor blade 12 (see FIG. 2), the retractor blade 12 can be disposed so as to at least partially cover the back opening 236 and thereby bound the proximal opening 222 in a backward direction. However, other configurations may be present.

As further illustrated, the distal opening 224 is laterally bound by the proximal and distal walls 226, 228 (though is less bounded by them than the proximal opening 222 is due to the change in angle of the guide 220 that occurs from the proximal to distal ends of the guide 220. The distal opening 224 is bounded toward the back by the floor 234. The distal opening 224 is immediately unbounded toward the front due to the distal opening 224 being contiguous with the front opening 232.

The relative proximal-distal positioning of the proximal opening 222 and the distal opening 224 on the modifies the operation of the shim 200 at least with respect to how the K-wire is controlled and how the K-wire (once inserted into the vertebral body) resists movement of the shim 200. Further, the proximal-distal positioning affects operation with respect to where the guide 220 directs the K-wire to enter the vertebral body. If the distal opening 224 is sufficiently proximal, the K-wire may miss the vertebral body endplate entirely and instead contact the outer shell of the vertebral body. In addition, the vertebral body is made from cancellous bone surrounded by a shell of cortical bone.

In the illustrated example, the guide 220 extends beyond the front face 201 of the shim 200. A proximal face of the guide 220 extends non-perpendicular to the front face 201 of the shim 200. In the illustrated example (see FIG. 7), the guide 220 does not extend laterally beyond bounds defined by the lateral edges of the front face of the shim 200. As illustrated, the guide 220 is curved in such a way that increases the angle θ relative to the midline axis of the shim 200. The curve of the guide 220 can not only facilitate changing a direction of the K-wire 98 but also facilitate wedging the relatively stiff K-wire 98 in place within the guide 220.

As illustrated, the anatomy connection section 293 further includes a single barb 294. The barb 294 can extend from a first side of the shim opposite a second side of the shim from which the K-wire 98 emerges. The barb 294 can be configured to resist removal of the shim 200 from a vertebral disc. The barb 294 can be elongate along a barb axis B in a direction substantially parallel to the guide axis G. As illustrated, the barb 294 has a blunt tip. In some examples, the barb 294 is generally bounded by the front and back faces of the shim 200. In other examples, the barb 294 is raised relative to the front face of the shim 200, which can further resist removal of the shim 200 once the barb 294 is inserted into the vertebral disc. The ends of the barb 294 along the barb axis can be relatively lower in height than a middle portion of the barb 294. The barb 294 can arch along its length. The barb 294 can have a proximal side 295 and a distal side 296. As illustrated, the proximal side 295 is relatively straight when viewed from the front, and the distal side 296 curves distally to approach parallel with the midline axis of the shim 200. In addition, the proximal side 295 is relatively more perpendicular to the front face of the shim 200 than the distal side 296, which is more sloped. Such a configuration can facilitate insertion of the barb 294 into the disc space and cause the barb 294 to resist withdrawal from the disc space.

In alternative implementations, the shim 200 may include no barbs or a plurality of barbs 294. In some examples, one or more barbs 294 on the shim 200 can be asymmetric with respect to other barbs 294. In some examples, in addition to or instead of the barbs 294, the shim 200 can include one or more serrations on one or both lateral sides of the shim 200.

While the shim 200 of FIG. 2 generally corresponds to the shim 200 described in more detail in relation to FIGS. 3-8. However, the shim can include one or more features of the shims described in FIGS. 9-20 or combinations thereof.

The distal portion of the shim 200 includes a barb 250 configured to resist removal of the shim 200 once inserted into a disc space. The barb 250 can include one or more aspects of the barb 294 described above. As illustrated, the barb 250 has a portion with a generally semicircular cross-section having a height that extends above a front face 201 of the shim 200. The height can reach below, the same level, or above the guide 220.

Second Example

FIGS. 9-14 show a second example shim 900. The shim 900 includes one or more features of the shim 200 but with some changes to the guide 220. Here, rather than being curved, the guide 220 is straight. In addition, the proximal end of the guide 220 includes a catch 402 extending at the proximal end. The catch 402 cooperates with a proximal end of the guide 220 to funnel the K-wire into the guide 220. For example, the catch 402 can be an extension of the distal wall 226 or a separate component.

Third Example

FIGS. 15-20 show a third example shim 1500. The third example shim 1500 includes one or more features of the first example shim 200 and the second example shim 900. In the illustrated example, the third example shim 1500. In this example, the guide 220 lacks a front opening, and the front opening extends through the entire guide 220 defining a T-shaped cross section of the path through the guide 220. The third example shim 1500 further includes a catch 402 as described above. The T-shaped path through the guide 220 can be made with a T-shaped tool such that the path can capture and retrain the K-wire. The size of the back opening 236 can be sufficiently small such that a retractor blade need not block the back opening 236 to prevent the K-wire from escaping the path in a rearward direction.

Method of Using the Shim

Figure 21:
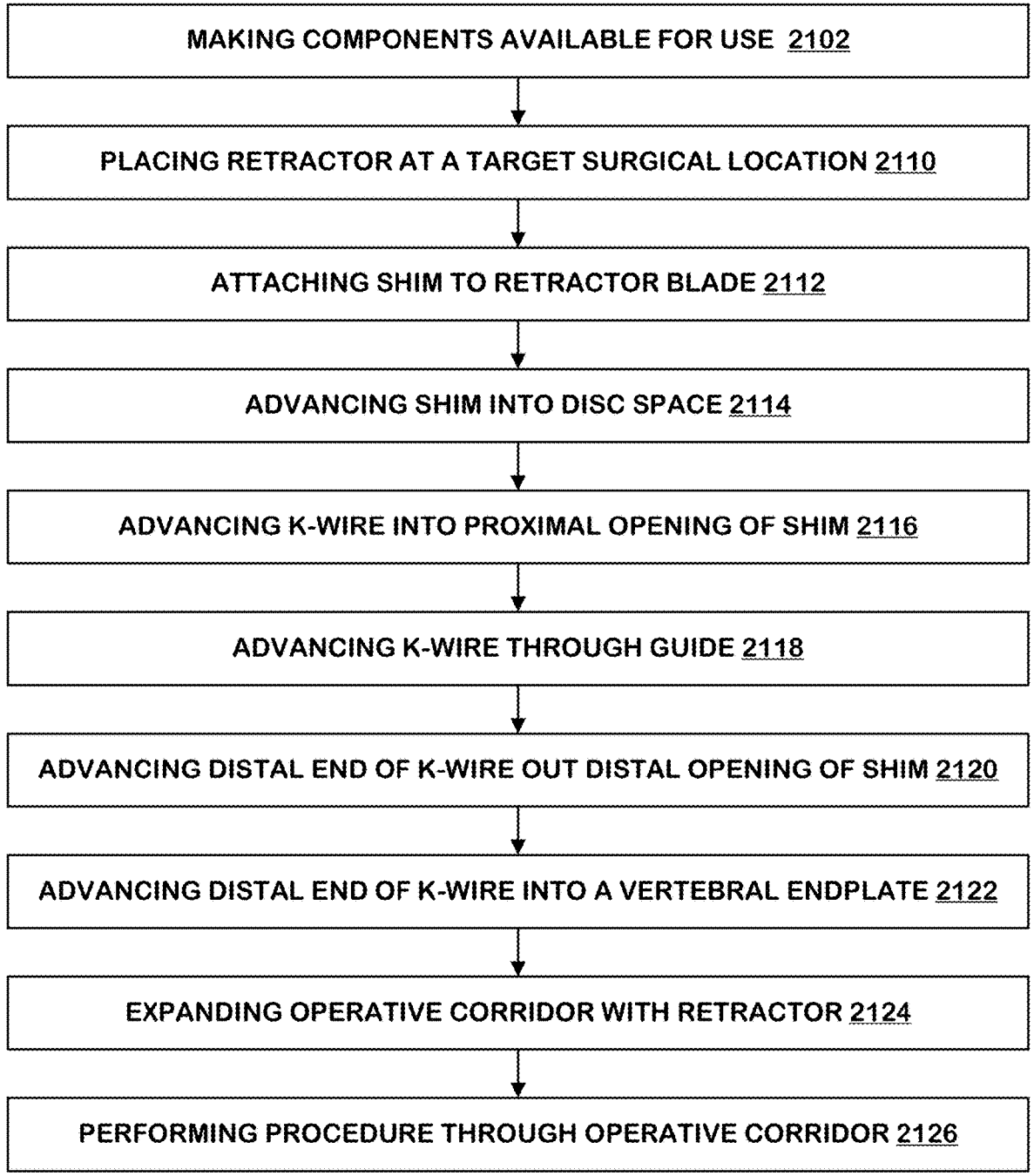
FIG. 21 illustrates an example method of using a shim.

FIG. 21 illustrates an example method 2100 of using the shim 200 during a spinal procedure. For ease of understanding, this method 2100 is described with reference to shim 200, though the method 2100 is applicable to other shims, including shim 900 and shim 1500. In an example, the procedure is a lateral interbody fusion procedure performed while the patient is in a prone position. The shim 200 can be used in other procedures, including, lateral interbody fusions, transforaminal interbody fusions, anterior lumbar interbody fusions, posterior interbody fusions, procedures at the cervical spine, procedures at the thoracic spine, procedures at the lumbar spine, procedures while the patient is in the prone position, procedures while the patient is in the supine position, procedures while the patient is in a lateral decubitus position, other procedures, or combinations thereof. The method can begin with operation 2102.

Operation 2102 includes making components available for use. The component can include any of the components described elsewhere herein, such as the retractor 10 and the shim 200, among others, variations thereof, and combinations thereof. In some examples, making available for use includes providing the parts of the components. The operation 2102 can include removing such components from sterile packaging and arranging them from use in an operating room.

Operation 2110 includes, during the spinal procedure, placing a retractor 10 in a target surgical location. The surgical location can be, for example, an intervertebral disc space at a spinal level where a procedure is to be performed. In an example, the operation 2110 can include advancing one or more blades of the retractor 10 over a dilation system such that a center retractor blade 12 is the posterior most blade of the retractor 10. Following operation 2110, the flow of the method 2100 can move to operation 2112.

Operation 2112 includes attaching a shim 200 to the retractor blade 12. For example, the shim 200 can be coupled to a shim inserter that is used to facilitate attaching the shim 200 to the retractor blade 12. The shim 200 can be placed at a proximal location of the retractor blade 12 and moved distally along a blade track of the retractor blade 12. The blade track can include dove tail grooves formed on the interior of blade that accommodate the tabs 208 along the shim 200. In some examples, the shim 200 can be attached to the retractor blade 12 prior to advancing the retractor to the target surgical location. The shim 200 can be coupled to the retractor blade 12 while the retractor is in a closed position. Following operation 2112, the flow of the method 2100 can move to operation 2114.

Operation 2114 includes advancing the shim 200 into the disc space. For example, the shim 200 is advanced along the retractor blade 12 until the distal end 204 of the shim 200 pierces the disc. The shim 200 continues to be advanced into the disc space such that the barb 294 (if any) is fully within the disc. The shim 200 can be advanced such that the distal opening 224 is within the disc. Following operation 2114, the flow of the method 2100 can move to operation 2116.

Operation 2116 includes advancing a K-wire 98 into the proximal opening 222 of the shim 200. In some examples, the K-wire 98 is advanced directly into the opening 222. In other examples, the K-wire 98 is guided (e.g., pushed, deflected, or otherwise moved) into the proximal opening 222 via one or more features, such as the catch 402. In some examples, the guide 220 or another portion of the shim 200 forms a funnel or other initial guide feature to direct the K-wire 98 into the proximal opening 222. The K-wire 98 can be initially advanced toward the opening 222 along an axis M perpendicular to a length of the shim 200. Following operation 2116, the flow of the method 2100 can move to operation 2118.

Operation 2118 includes advancing the K-wire 98 through the guide 220. The advancing the K-wire 98 through the guide 220 can include causing or permitting the guide 220 to bend the K-wire 98 such that the distal end of the K-wire 98 follows a guide axis G, such as by bending the K-wire 98 by θ degrees relative to a midline axis M. The operation 2118 can include bending the K-wire 98 toward a vertebral endplate. The operation 2118 can include bending the K-wire 98 away from the barb 294. The operation 2118 can include bending the K-wire 98 in a single plane (e.g., a plane parallel to the side-side axis of the shim 200. The operation 2118 can include bending the K-wire 98 in multiple planes. The operation 2118 can include bending the K-wire 98 away from the barb 94. The operation 2118 can include bending the K-wire 98 cranially or caudally. Following operation 2118, the flow of the method 2100 can move to operation 2120.

Operation 2120 can include advancing a distal end of the K-wire 98 out of the distal opening 224. In many examples, the K-wire 98 exits the distal opening 224 and directly enters the disc. Following operation 2110, the flow of the method 2120 can move to operation 2122.

Operation 2122 can include advancing the distal end of the K-wire 98 into a vertebral endplate. Sufficient amounts of the K-wire 98 can be advanced into the vertebral body to facilitate securing the shim 200 and thereby secure the retractor blade 12 coupled to the shim 200. In this manner, the K-wire 98 resists movement of the coupled blade, such as posteriorly towards nerve tissue located in the posterior portion of the psoas muscle. Following operation 2122, the flow of the method 2100 can move to operation 2124.

Operation 2124 can include expanding the operative corridor with the retractor 10. For example, the retractor blades 12, 16, and 18 are separated, providing an operative corridor through which instruments or implants can be advanced to the target site. Following operation 2124, the flow of the method 2100 can move to operation 2126.

Operation 2126 can include performing one or more procedures through the operative corridor. Any number of procedures may be performed on the spine through the lateral access corridor, such as a fusion procedure, a total disc replacement, or a corpectomy, among other procedures.

Method of Manufacturing the Shim

FIG. 22 illustrates an example method 2200 by which the shim 200 is manufactured. For ease of understanding, this method 2200 is described with reference to shim 200, though the method 2200 is applicable to other shims, including shim 900 and shim 1500. In this example, the shim 200 is formed at least partially through subtractive manufacturing where the shim 200 is constructed from a metal or other material and the material is removed to define the features of the shim 200. In other examples, the shim 200 is formed via an additive or other manufacturing process. The method can begin with operation 2210.

Operation 2210 includes forming the guide 220, in part, through one or both of a front opening 232 and a back opening 236. In some examples, the operation 2210 can include forming the front opening 232 and the back opening 236 concurrent with forming the guide 220. At least some portions of the guide 220 need not be formed through the front opening 232 and the back opening 236. In some examples, the operation 2210 include forming the roof 230 at least in part by forming a blind opening from the back of the shim 200. In some examples, the operation 2210 includes forming the floor 234 of the guide 220 by forming a blind opening through the front opening 232. In some examples, there are through connections that connect the front opening 232 and the back opening 236. In some examples, such as when forming shim 1500, no front opening 232 is formed and, instead, the entirety of the path 223 is formed through the back opening 236. The resulting formation can include forming a substantially T-shaped path through the back guide 220.

Operation 2212 includes forming one or more additional features. The additional features can be additional features of the guide 220 or other portions or shapes of the shim 200 as described above in any of the figures.

Radiographic Image of Shim

Figure 23:
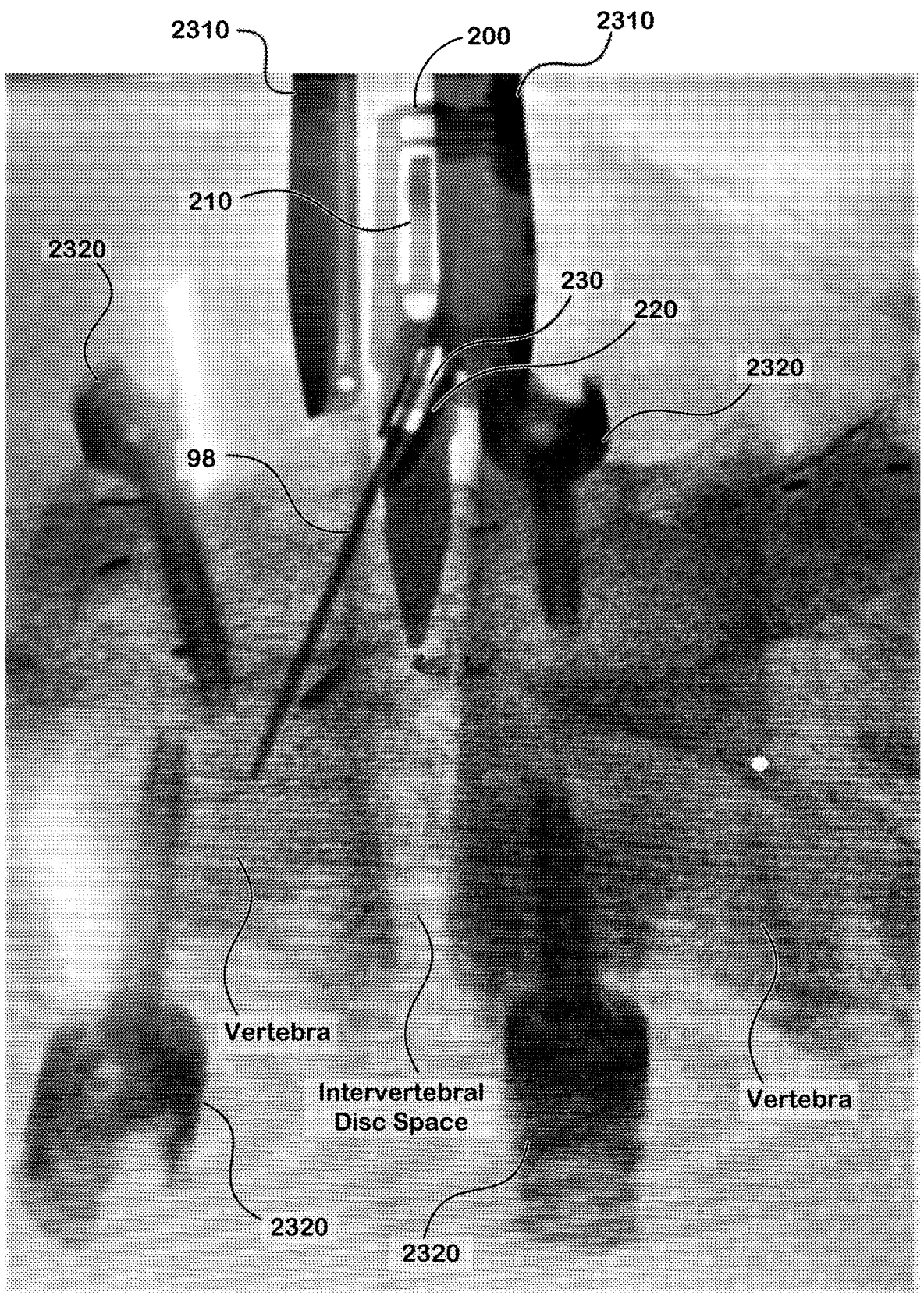
FIG. 23 illustrates a radiographic image of a shim.
Figure 26:
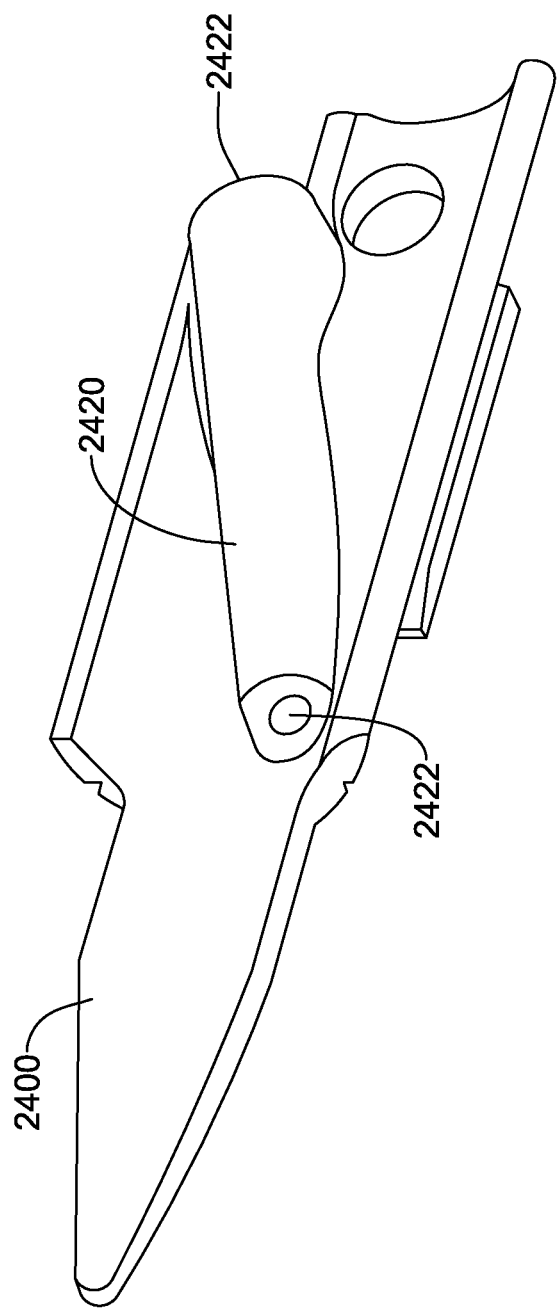
FIG. 26 illustrates a front perspective view of a prior shim.

FIG. 23 illustrates a radiographic image of a working model of the shim 200 disposed in an intervertebral disc space between adjacent vertebrae. The shim 200 is coupled to a substantially radiolucent medial retractor blade between adjacent additional retractor blades. A K-wire 98 is guided through the guide 220 and into a vertebral endplate of an adjacent vertebra. Bone anchors 2220 are anchored into the vertebrae.

Any of the features or attributes of the above described embodiments and variations can be used in combination with any of the other features and attributes of the above described embodiments and variations as desired. Various modifications, additions and other alternative embodiments are possible without departing from the true scope and spirit. The embodiments presented herein were chosen and described to provide an illustration of various principles of the present invention and its practical application to thereby enable one of ordinary skill in the art to utilize the invention in various embodiments and with various modifications as are suited to the particular use contemplated. All such modifications and variations are within the scope of the present invention as determined by the appended claims when interpreted in accordance with the benefit to which they are fairly, legally, and equitably entitled.

What is claimed is:

1. A surgical shim comprising:
   a length defining a midline axis;
   a front surface;
   a back surface opposite the front surface;
   a retractor connector;
   a guide disposed at the front surface, wherein the guide defines:
      a proximal opening;
      a distal opening;
      a path from the proximal opening to the distal opening extending along a guide axis oblique to the midline axis; and
      a back opening extending through the front surface and the back surface; and
   a K-wire extending through the guide along the path.

2. The surgical shim of claim 1, wherein the guide further defines a front opening.

3. The surgical shim of claim 1, wherein the guide further includes a roof.

4. The surgical shim of claim 3, wherein the guide further includes:
   a proximal wall; and
   a distal wall,
   wherein the roof spans at least part of the proximal wall and the distal wall.

5. The surgical shim of claim 4, wherein the roof covers a portion of the back opening.

6. The surgical shim of claim 4, wherein at least a portion of a floor of the guide between the proximal wall and the distal wall is not covered by the roof.

7. The surgical shim of claim 4, wherein no portion of the guide along the path is covered by both a floor and the roof when viewed from the front of the surgical shim.

8. The surgical shim of claim 1,
   wherein the distal opening is disposed proximate a first side of the shim; and
   wherein the surgical shim further comprises:
      a barb disposed proximate a second side of the shim opposite the first side.

9. The surgical shim of claim 8,
   wherein the barb is the only barb of the shim;
   wherein the barb has a proximal side extending parallel to a guide axis of the guide;
   wherein the proximal side of the barb has a steeper slope than a distal side of the guide; and
   wherein a maximum height of the barb above the front surface of the shim is the same as a maximum height of the guide above the front surface of the shim.

10. The surgical shim of claim 1, wherein the surgical shim is coupled to a retractor blade via the retractor connector.

11. A system comprising:
    the surgical shim of claim 1; and
    an implant.

12. An apparatus comprising:
    a K-wire;
    a retractor blade; and
    a surgical shim having a midline axis along a length of the surgical shim, the surgical shim comprising:
       a front surface;
       a back surface opposite the front surface;
       a retractor connector coupled to the retractor blade; and
       a guide disposed at the front surface and having a floor, wherein the guide defines:
          a proximal opening;
          a distal opening;
          a path from the proximal opening to the distal opening that extends along a guide axis oblique to the midline axis; and
          a back opening through the floor to the back surface, wherein the back opening is at least partially covered by the retractor blade; and wherein the K-wire extends through the guide along the path.

13. The apparatus of claim 12, further comprising:
a retractor,
wherein the retractor blade is coupled to the retractor.

14. The apparatus of claim 12,
wherein the shim further comprises:
   a proximal wall;
   a distal wall; and
   a roof spanning at least part of the proximal wall and the distal wall,
      wherein the roof does not cover the floor when the shim is viewed from the front.

15. The apparatus of claim 12, further comprising:
an implant.

16. A method comprising:
making available for use a surgical shim and a retractor having a retractor blade;
placing the retractor blade at a target surgical location;
attaching the surgical shim to the retractor blade, wherein attaching the surgical shim to the retractor blade is performed such that a back opening of the guide is at least partially blocked by the retractor blade;
advancing the surgical shim into a disc space such that a distal opening of a guide of the surgical shim is disposed within the disc space;
advancing a K-wire into a proximal end opening of the guide;
advancing the K-wire through the guide and out the distal opening of the guide;
expanding an operative corridor with the retractor; and
performing a procedure through the operative corridor.

17. The method of claim 16, further comprising:
advancing the K-wire into a vertebral endplate.

18. The method of claim 16, wherein the procedure is a prone lateral interbody fusion.

19. The method of claim 16, wherein advancing the K-wire through the guide and out the distal opening of the guide includes:
wedging the K-wire in a curved section of the guide.

20. The method of claim 16, wherein performing the procedure through the operative corridor includes:
advancing an implant through the operative corridor to a target site.

21. A surgical shim comprising:
a front surface;
a back surface opposite the front surface;
a retractor connector; and
a guide disposed at the front surface,
wherein the guide defines:
   a proximal opening;
   a distal opening;
   a path from the proximal opening to the distal opening; and
   a back opening extending through the front surface and the back surface;
wherein the guide includes:
   a proximal wall;
   a distal wall; and
   a roof spanning at least a portion of the proximal wall and at least a portion of the distal wall; and
wherein the roof covers at least a portion of the back opening.

22. The surgical shim of claim 21,
wherein the path extends along a guide axis oblique to a midline axis along the length of the surgical shim.

23. The surgical shim of claim 21, further comprising:
a K-wire extending through the guide.

24. The surgical shim of claim 21, wherein the guide further defines a front opening.

25. The surgical shim of claim 21, wherein at least a portion of a floor of the guide between the proximal wall and the distal wall is not covered by the roof.

26. The surgical shim of claim 21, wherein no portion of the guide along the path is covered by both a floor and the roof when viewed from the front.

27. The surgical shim of claim 21,
wherein the distal opening is disposed proximate a first side of the shim; and
wherein the surgical shim further comprises:
   a barb disposed proximate a second side of the shim opposite the first side.

28. The surgical shim of claim 27,
wherein the barb has a proximal side extending parallel to a guide axis of the guide;
wherein the proximal side of the barb has a steeper slope than a distal side of the guide; and
wherein a maximum height of the barb above the front surface of the shim is the same as a maximum height of the guide above the front surface of the shim.

29. The surgical shim of claim 21, wherein the surgical shim is coupled to a retractor blade via the retractor connector.

30. A system comprising:
the surgical shim of claim 21; and
an implant.

31. A surgical shim comprising:
a front surface;
a back surface opposite the front surface;
a retractor connector;
a guide disposed at the front surface, wherein the guide defines:
   a proximal opening;
   a distal opening disposed proximate a first side of the shim;
   a path from the proximal opening to the distal opening; and
   a back opening extending through the front surface and the back surface; and
a barb disposed proximate a second side of the shim opposite the first side,
wherein the barb is the only barb of the shim;
wherein the barb has a proximal side extending parallel to a guide axis of the guide;
wherein the proximal side of the barb has a steeper slope than a distal side of the guide; and
wherein a maximum height of the barb above the front surface of the shim is the same as a maximum height of the guide above the front surface of the shim.

32. The surgical shim of claim 31,
wherein the path extends along a guide axis oblique to a midline axis along the length of the surgical shim.

33. The surgical shim of claim 31, further comprising:
a wire extending through the guide.

34. The surgical shim of claim 31, wherein the guide further defines a front opening.

35. The surgical shim of claim 31, wherein the guide further includes a roof.

36. The surgical shim of claim 35, wherein the guide further includes:

a proximal wall; and a distal wall, wherein the roof spans at least part of the proximal wall and the distal wall.

37. The surgical shim of claim 36, wherein the roof covers a portion of the back opening.

38. The surgical shim of claim 36, wherein at least a portion of a floor of the guide between the proximal wall and the distal wall is not covered by the roof.

39. The surgical shim of claim 36, wherein no portion of the guide along the path is covered by both a floor and the roof when viewed from the front.

40. The surgical shim of claim 31, wherein the surgical shim is coupled to a retractor blade via the retractor connector.

* * * * *